United States Patent [19]

Mosier et al.

[11] Patent Number: 4,766,065
[45] Date of Patent: Aug. 23, 1988

[54] DETECTION OF CELL MEMBRANE PROTEIN

[75] Inventors: Larry Mosier, St. Louis; John Petersen, Creve Cover, both of Mo.

[73] Assignee: Becton Dickinson and Company, Franklin Lakes, N.J.

[21] Appl. No.: 643,403

[22] Filed: Aug. 23, 1984

[51] Int. Cl.$^4$ .................... G01N 33/53; C12Q 1/04
[52] U.S. Cl. ............................................. 435/7; 435/34
[58] Field of Search ............... 435/7, 34, 803, 820, 435/259; 436/510, 524, 527, 528, 533, 534, 804, 543

[56] References Cited

U.S. PATENT DOCUMENTS

| | | | |
|---|---|---|---|
| 3,855,197 | 12/1974 | Hirsch et al. | 435/803 X |
| 3,891,508 | 6/1975 | Merrick | 435/34 |
| 4,118,469 | 10/1978 | Caldwell et al. | 436/516 |
| 4,427,782 | 1/1984 | Caldwell et al. | 436/542 |
| 4,497,899 | 2/1985 | Armstrong et al. | 436/811 X |

*Primary Examiner*—Robert J. Warden
*Assistant Examiner*—Randall E. Deck
*Attorney, Agent, or Firm*—James R. McBride

[57] ABSTRACT

The invention comprises a method for detecting cell proteins of microorganisms, such as the principal outer membrane protein of *Chlamydia trachomatis* having a mean molecular weight of 39,500 daltons. The method includes the steps of adding a buffer salt solution to a specimen suspected of containing bacterial antigens, raising the pH of the buffered solution so produced, incubating the solution, adding a neutralizing buffer to the solution to lower the pH, and assaying the sample by conventional immunoassay techniques. Optionally the sample solution is heated prior to incubation and then cooled afterwards before adding the neutralizing buffer.

15 Claims, No Drawings

DETECTION OF CELL MEMBRANE PROTEIN

TECHNICAL FIELD

This invention relates generally to the detection of the cell proteins of microorganisms. Of particular interest is the detection of the principal outer membrane protein of *Chlamydia trachomatis*. Because this protein exhibits antigenic properties common to all the *Chlamydia trachomatis* serotypes, its detection is useful as a diagnostic indicator.

BACKGROUND OF THE INVENTION

Immunoassay is in many cases the method of choice for detecting infection by microorganisms. As an aid to specific diagnosis, the assay must be capable of identifying a particular species of microorganism with a high degree of reliability. In most cases this requires the isolation of species specific antigens for reaction with appropriate antibodies. Typical of the type of organism yielding to such analysis is *Chlamydia trachomatis*, which is one of the two microorganism species of the genus Chlamydiaceae, order Chlamydiales. The other species is *Chlamydia psittaci*. *Chlamydia trachomatis*, in its some fifty various strains, are the etiologic agents for a number of human ocular and genital diseases including trachoma, inclusion conjunctivitis, lymphogranuloma venereum, "nonspecific" or nongonococcal urethritis and proctitis. *C. trachomatis* infection is pervasive throughout the general population. It has been estimated, for instance, that *C. trachomatis* is accountable for several million cases per year of nongonococcal urethritis.

Since *C. trachomatis* mediated disease is widespread, a reliable, simple and inexpensive test for the organism's presence is highly desirable and of great importance in order that proper treatment can be undertaken. The only serological test in current use is the microimmunofluorescence test. This test however requires that the strains of *C. trachomatis* be used as serological test antigen. In addition, the facilities for conducting this test are available in only a limited number of laboratories throughout the world. The test is very laborious, time consuming and difficult to perform.

Recently, U.S. Pat. No. 4,118,469, noted the preparation of an antigen of *C. trachomatis* useful in serological testing for lymphogranuloma venereum and nongonococcal urethritis. Such antigen was purified from *C. trachomatis* organisms by immunoadsorption chromatography using the monospecific antiserum as a specific ligand covalently bound in an agarose gel column. This antigen had a molecular weight of only about 160,000 daltons, and in counter-immunoelectrophoresis testing was capable of detecting antibodies from the sera of lymphogranuloma venereum patients. However, when utilized in a similar test with sera of nongonococcal urethritis patients, this antigen failed to detect antibodies. It was successful, however, in detecting antibodies in two dimensional immunoelectrophoresis testing.

In any event, however, there is still great medical interest in the isolation of species specific antigens of microorganisms, such as *C. trachomatis*, which are capable of detecting infection, preferably by commonly practiced antigen-antibody assay methods. It therefore is an object of the present invention to provide an improved method of isolating such species specific antigens.

BRIEF SUMMARY OF THE INVENTION

The present invention relates to a diagnostic testing method for detecting cell proteins. Although the invention is described in detail with reference to *Chlamydia trachomatis*, it is to be understood that the invention applies equally to cell membrane proteins of microorganisms in general.

In many microorganisms cell membrane proteins are species-specific antigens. That is, when tested against antibodies derived from all the sera types of the microorganism, the protein reacts with species specificity. The protein thus is a unique protein common to all serotypes of the microorganism, and as an antigen, provides a basis for the identification of all such serotypes.

The method of this invention for releasing cell membrane proteins from a microorganism includes the steps of: taking a test sample suspected of containing a particular microorganism, mixing the sample with a first buffer solution having a pH of from about 6.0 to about 8.0, forming a sample solution thereby, adjusting the sample pH to a value of from about 8.0 to about 12.5 using a solution of base, incubating the sample for a period of from about 5 minutes to about 30 minutes, adding a neutralizing second buffer having a pH of from about 1.0 to about 7.0 to bring the pH of the sample to a final value of from about 7.0 to about 8.0, and assaying the sample to detect the presence of antigens.

In a specific embodiment of this invention, a test method for releasing the principal outer membrane protein from *C. trachomatis* includes: taking a sample such as a cervical or urethral test swab, placing the sample in a first buffer solution comprising sucrose phosphate having a pH of about 7.0, mixing the swab with the buffer solution to form a sample solution, adding to the sample solution a quantity of sodium hydroxide solution having a molarity of about 0.4, thereby raising the pH of the sample solution to between about 11.0 and about 11.8, raising the temperature of the sample solution to about 100° C., incubating the sample solution for a period of about 15 minutes, cooling the sample solution to a temperature of from about 20° C. to about 30° C., reducing the pH of the cooled sample solution to between about 7.2 and about 7.8 using a neutralizing buffer of phosphate having a pH of about 6.1, and assaying the sample to detect the presence of antigens.

DETAILED DESCRIPTION OF THE INVENTION

Cell membrane proteins of many microorganisms of interest are species-specific antigens to all serotypes of those organisms. One such protein is the principal outer membrane protein of *Chlamydia trachomatis*. This protein comprises about 60% of the total associated outer membrane protein of *C. trachomatis*, and has a size or subunit molecular weight of between about 30,000 and about 44,000 daltons, with a mean molecular weight of about 39,500 daltons. Hereinafter for ease in reference, this principal outer membrane protein group will be referred to as MP 39.5, signifying "major outer membrane protein having a mean subunit molecular weight of 39,500 daltons".

The detection of a cell membrane protein is indicative of infection with that microorganism in an individual. Effective detection requires that the protein be released and/or exposed from within the infective particle of a microorganism cell. Once this is done, detection may be accomplished by a variety of assays, for example, radioimmunoassay (RIA), enzyme linked immunosorbent assay (ELISA), etc.

In accordance with the method of the present invention, disclosed is a procedure for treatment of the infective particles in cells of microorganisms, which involves the taking of a sample or specimen suspected of harboring the organism, and subjecting the sample to an alkali solution and optionally heat.

Applicant has discovered that treating cells with an alkali solution will release and/or expose cell membrane proteins from the infective particle of the cell. Applicant further has discovered that the addition of heat to the treatment process increases the efficiency by which the protein is released and/or exposed. Various assays then can be conducted to detect the presence of the protein in a sample containing the treated cells.

A general procedure in accordance with this invention is as follows: a test sample is first mixed with a buffer salt solution having a pH of from about 6.0 to about 8.0. Suitable buffers include sugar phosphate buffers, such as sucrose phosphate, and other sugar-containing buffers known to the art. Desirably, the pH of the buffer solution is from about 6.8 to about 7.2.

After the sample and the buffer salt solution have been mixed thoroughly, a quantity of alkali solution is added to the sample to raise the pH to between about 8.0 and about 12.5. Desirably the pH is from about 10.0 to about 12.0, with from about 11.0 to about 11.8 preferred. Suitable alkali solutions include those of sodium hydroxide, potassium hydroxide, trisodium phosphate, and tri(hydroxymethyl)aminomethane, with sodium hydroxide being preferred.

Once the pH has been adjusted to the desired level, the sample is incubated for a period of from about 5 to about 30 minutes. The incubation can take place at room temperature (20° C.) or at elevated temperatures up to about 105° C. Desirably, the temperature of the sample is raised to between about 90° C. and about 100° C., with about 100° C. preferred. The use of elevated temperatures during the incubation has been found to increase the efficiency by which the cell membrane protein is released and/or exposed. After the incubation period, if the sample solution has been heated, it is cooled to a temperature of from about 0° C. to about 40° C., with about 25° C. preferred. Cooling is preferably by immersion in an ice bath.

After cooling the sample, a neutralizing second buffer is added, having a pH of from about 1.0 to about 7.0, to bring the pH of the sample to a final value of from about 7.0 to about 8.0. Optimum conditions for assaying are generally obtained at these pH values, i.e., neutral to slightly alkaline. Preferably the solution has a final pH of from about 7.2 to about 7.8. Suitable neutralizing buffers include the various phosphate buffer solutions (PBS), with sucrose phosphate preferred. Other suitable buffer solutions include citric acid, hydrochloric acid and tri(hydroxymethyl)aminomethane.HCl. Following this pH adjustment, the sample is ready for assaying without further modification.

As is apparent from the preceding description, a variety of buffer salts, alkali solutions to raise the pH, and neutralizing buffers can be used in the method of this invention, along with a broad range of incubation times and temperatures. The actual reaction components and conditions can be selected so as to integrate the method of liberating MP 39.5, or other protein, into the particular detection assay of interest, e.g., enzyme immunoassay (EIA), radioimmunoassay (RIA), latex immunoassay, etc. In general, any type of known immunoassay technique can be used.

Monospecific antibodies against, for example, MP 39.5 antigen can be generated by suitable inoculation procedures with laboratory animals such as mice or rabbits. The animal generated antibodies may be utilized in assays for Chlamydial infection in other mammals. These assays may be conducted using well-known procedures for assaying the presence of bacterial antigen in the infected subject. Once a supply of monospecific antibodies has been secured from MP 39.5 antigen-inoculated laboratory animals, either direct or indirect assay procedures can be undertaken using specimens suspected of harboring Chlamydial infections.

In a direct assay procedure, monospecific antibody against the membrane protein may be covalently or noncovalently attached to a solid phase support system. As is customary in these techniques, the support system may be glass plastic or the like.

The solid phase support with attached monospecific antibody against the particular membrane protein may be incubated with a specimen prepared as outlined above. Monospecific antibody against the membrane protein antigen, which previously has been radiolabeled or conjugated with enzyme by known techniques, is then equilibrated against the support system. Any antigen present in the specimen and which has been bound to the antibody on the support system will in turn bind to the radiolabeled or enzyme conjugated antibody.

If radiolabeled antibody is used, the amount of residual radioactivity in the sample then may be determined. This value is compared to specimens that have been determined to be free of the membrane protein antigen. In the event enzyme conjugated antibody is used, a substitute specific for the enzyme is added to the solid support reaction mixture and the resultant color change is recorded spectrophotometrically. This color change is compared to samples known to be free of the membrane protein antigen. In this way, the presence of the antigen in specimens can be assayed directly.

Alternatively, indirect assay procedures can be used. Specifically, the antigens can be covalently or noncovalently bound to a suitable solid phase support system. A specimen prepared as outlined above is mixed with a known quantity of radiolabeled or enzyme conjugated antibody against the membrane protein antigen, previously secured from a laboratory animal source. The specimen extract-antibody mixture may then be incubated with the solid support system and its bound antigen.

The radioactivity of the solid support system is measured, or color development in the conjugated system is measured, and compared to specimens similarly treated as standards and which do not contain the antigen of interest.

The ability of the clinical sample suspected of containing the microorganism to inhibit the binding of the radiolabeled or enzyme conjugated antibodies to the solid support reveals the presence, or absence, of the membrane protein antigen in the clinical specimen. Any demonstrated inhibition indicates infection. Other suitable assay methods and variations will be apparent to those skilled in such assay techniques.

The following example illustrates the invention as applied to the detection of *Chlamydia trachomatis* MP 39.5. With little or no modification, the described procedure can be used for detection of other types of cell proteins in a variety of microorganisms.

EXAMPLE

One hundred clinical swabs were obtained and tested for the presence of Chlamydia. Reagent formulations were prepared as follows:

A. Sodium Hydroxide (0.42 M) Solution
34 ml 50% (12.5 M) NaOH
q.s. to 1.0 L

B. Neutralizing Buffer
to 900 mL dH$_2$O add:
NaH$_2$PO$_4$.H$_2$O 13.8 g
adjust pH to 6.10 ± 0.05 with NaOH
BSA      2.0 g
NaN$_3$   1.0 g

C. Standard Diluent
to 800 ml dH$_2$O add:
| 6.90 g | NaH$_2$PO$_4$.H$_2$O |
| 1.000 g | BSA |
| 0.50 g | NaN$_3$ |
| 34.25 g | Sucrose |
| 1.044 g | K$_2$HPO$_4$ |
| 0.544 g | KH$_2$PO$_4$ |
| 25.0 ml | Heat Treated Fetal Calf Serum |
| 25 mg | Streptomycin |
| 50 mg | Vancomycin |
| 12,500 units Nystatin | | adjust pH to 7.45 ± 0.05 using 0.42 M NaOH
q.s. to 1.0 L
Filter through a 0.22 um filter

D. Conjugate Buffer
to 600 ml dH$_2$O add:
| 0.532 g | KH$_2$PO$_4$ |
| 2.80 g | K$_2$HPO$_4$ |
| 0.20 g | Thimerosal |
| 250. ml | Heat Teated Fetal Calf Serum | adjust pH to 7.4 ± 0.1
q.s to 1.0 L
Filter through 0.22 um filter

E. Well Wash Buffer
to 900 ml dH$_2$O add:
| 0.532 g | KH$_2$PO$_4$ |
| 2.800 g | K$_2$HPO$_4$ |
| 1.000 g | BSA | adjust pH to 7.4 ± 0.1
q.s. to 1.0 L with dH$_2$O

F. Substrate Buffer
to 900 ml dH$_2$O add:
8.203 g Sodium Acetate Anyhdrous
adjust pH with 1 M Citric Acid to 6.0 ± 0.1
q.s. to 1.0 L with dH$_2$O

G. Tetramethyl Benzidine (TMB) Substrate
to 900 ml Dimethyl Sulfoxide (DMSO) - Spectragrade, freezing point, 18° C. add:
10.0 g 3,3',5,5', tetramethyl benzidine
q.s. to 1.0 L with DMSO.
Store at room temperature

H. 0.5 M Hydrogen Peroxide Solution
to 500 ml stabilized 3% H$_2$O$_2$ add 500 ml
dH$_2$O and mix.

I. Stopping Solution - 2 M Sulfuric Acid
to 800 ml dH$_2$O add:
carefully 111 ml Sulfuric Acid (concentrated).
Cool to R.T.
q.s. to 1.0 L with dH$_2$O

J. 2 SP Transport Media
to 900 ml dH$_2$O add:
| Sucrose | 68.5 g |
| K$_2$HPO$_4$ | 2.088 g |
| KH$_2$PO$_4$ | 1.088 g |
| Fetal Calf Serum (Heat Treated) 50 ml | |
| Streptomycin | 50 mg |
| Vancomycin | 100 mg |
| Nystatin | 25,000 units |

Adjust pH to 7.0 and q.s. to 1.0 L
filter through sterile 0.22 um filter.

Sample Treatment

Sample dacron swabs were cut just above cotton directly into 10×75 mm glass test tubes. Two tubes were also set up with unused swabs as blanks. 500 ul of 2SP transport medium was added to each tube and the mixtures vortexed 10–20 seconds vigorously, followed by addition of 50 ul 0.42 M NaOH to each tube. The mixtures were then vortexed 10–20 seconds vigorously, followed by incubation at 100° C. (±2° C.) for 15 minutes. The tubes were then placed in an ice bath and cooled to about 25° C., after which 500 ul of the neutralizing buffer were added. The mixtures were then vortexed 10–20 seconds vigorously. Samples were then ready for assay.

Assay Protocol—Enzyme Linked Immuo-sorbent Assay(ELISA)

Antibody coated plates were washed 3 times with wash buffer and tapped dry. One hundred microliters of standards, controls, blanks or treated samples were added to corresponding duplicate wells, followed by mixing. The controls were sample swabs known to contain elementary bodies of Chlamydia and treated as described above. A second set of controls known to contain elementary bodies were treated with 500 ul of the neutralizing buffer and 50 ul NaOH. This set of controls was untreated. The plates were then covered with plate sealers (tin foil) and incubated overnight at ambient temperature. The contents of the wells were then discarded and the plates again washed, as above. One hundred microliters of conjugate were added to each well, followed by mixing and covering with plate sealers. The plates were then incubated at 37° C. for 2 to 3 hrs. The contents of the well were again discarded and the plate washed, as above, followed by the addition of two hundred microliters of working TMB substrate solution. The working solution had the following composition:

10.0 ml Substrate buffer
100 ul Stock TMB substrate
30 ul 0.5M H$_2$O
Mix solution thoroughly The mixture was incubated 30 minutes at ambient temperature with occasional mixing. The reaction was then stopped by the addition of 50 microliters of 2M H$_2$SO$_4$. The plates were read against a substrate blank prepared by adding 200 microliters substrate and 50 microliters 2 M H$_2$SO$_4$ to a strip of wells, using a 450 nanometer filter.

Calculations and Interpretation of Results

The absorbance of the blank swabs should be comparable to the 0.0ng/ml standard. Absorbances of standard wells, controls and samples were each averaged. The average 0.0ng/ml absorbance was subtracted from all averaged absorbances of standards. The average absorbance of the blank swabs was subtracted from the average absorbances of all samples and controls. The corrected average absorbance of each standard was then plotted against the concentration in ng/ml, and the recoveries determined from the plotted curves. A recovery value of ≧0.5 ng/ml was considered positive.

All positive samples were repeated using both the above protocol and the confirmatory assay given below.

Confirmatory Assay Protocol for Positive Samples

Using the same Chlamydia antibody coated on the ELISA wells, solutions were prepared containing 1 mg/ml in standard buffer diluent. 10×75 mm test tubes were labeled by adding 250 ul of each digested positive sample or control to be treated. 5 ul of the antibody solution were added to all tubes, which were then mixed thoroughly by vortexing and left standing for 5 minutes. To corresponding duplicate wells were added 100 ul of the antibody treated samples. Duplicate wells from aliquots of the digested samples were also set up (not treated with Ab). Assays were then performed as described above.

Interpretation of Results from Confirmatory Testing

A positive result was assigned to samples with MP 39.5 recoveries ≧0.5 ng/ml in the wells containing the samples not treated with antibody and a significant decrease (>70% inhibition) in recovery in the sample treated with antibody. A sample assaying as positive or questionable positive when first assayed that becomes negative in the confirmatory assay was considered negative. This may result either from recovering ≦0.5 ng/ml on the repeat test (aliquots not treated with Ab) or where the aliquots treated with antibody did not show a significant decrease in recovery.

Results

Of the 100 samples tested, 62 were negative and 38 positive. Confirmation of positive results was by inhibition assay. Elementary bodies (EB) in controls were divided into treated and untreated groups to determine the efficiency of MP 39.5 liberation. Of the treated EB the average absorbance at 450 nanometers was 0.611 while the untreated EB yielded an absorbance of 0.018 at 450 nanometers.

We claim:

1. A method for detecting cell membrane proteins of *Chlamydia trachomatis*, comprising:
   taking a test sample suspected of containing *Chlamydia trachomatis*;
   mixing the sample with a first buffer solution having a pH of from about 6.0 to about 8.0, forming a sample solution thereby;
   adjusting the sample solution pH to a value of from about 8.0 to about 12.5 using a solution of base;
   incubating the sample solution for a period of from about 5 minutes to about 30 mintues;
   adding a neutralizing second buffer having a pH of from about 1.0 to about 7.0 to bring the pH of the sample solution to a final value of from about 7.0 to about 8.0; and
   assaying the sample solution to detect the presence of antigens of *Chlamydia trachomatis*.

2. The method of claim 1 wherein the first buffer is selected from the group consisting of solutions of sugar-coated buffers.

3. The method of claim 2 wherein the base is selected from the group consisting of sodium hydroxide, KOH, trisodium phosphate, and tri(hydroxymethyl)aminomethane.

4. The method of claim 3 wherein said method further includes heating the sample solution to a temperature of from about 20° C. to about 105° C. after said adjusting of the sample pH, incubating the sample solution at that temperature, and cooling the sample solution after incubation to between about 0° C. and about 40° C.

5. The method of claim 4 wherein the first buffer is sucrose phosphate.

6. The method of claim 5 wherein said heating is to a temperature of from about 90° C. to about 100° C.

7. The method of claim 6 wherein the neutralizing second buffer is selected from the group consisting of solutions of phosphates, citric acid, hydrochloric acid and tri(hydroxymethyl)aminomethane HCl having a pH of from about 1.0 to about 7.0.

8. The method of claim 7 wherein said final pH of said sample solution is from about 7.2 to about 7.8.

9. The method of claim 8 wherein said adjusting of the pH of the sample solution is to between about 11.0 and 11.8.

10. The method of claim 9, wherein the base is sodium hydroxide.

11. The method of claim 10, wherein said cooling of the sample solution is to about 25° C.

12. The method of claim 11, wherein the neutralizing second buffer is sucrose phosphate.

13. The method of claim 12, wherein the assay is a radioimmunoassay.

14. The method of claim 12, wherein the assay is an enzyme linked immunoabsorbent assay.

15. A method for detecting the principal outer membrane protein of *Chlamydia trachomatis*, comprising:
   taking a sample; placing the sample in a buffer solution comprising sucrose phosphate having a pH of about 7.0;
   mixing the sample with the buffer solution to form a sample solution;
   adding to the sample solution a quantity of sodium hydroxide solution having a molarity of about 0.4 to thereby raise the pH of the sample solution to between about 11.0 and 11.8;
   raising the temperature of the sample solution to about 100° C.;
   incubating the sample solution at said temperature for a period of about 15 minutes;
   cooling the sample solution to a temperature of from about 20° C. to about 30° C.;
   reducing the pH of the cooled sample solution to between about 7.2 and 7.8, using a neutralizing buffer of phosphate having a pH of about 6.1; and
   assaying the sample solution to detect the presence of the out